Sept. 5, 1944. A. DICKSON, JR Plant Pat. 638
ROSE PLANT
Filed April 25, 1944
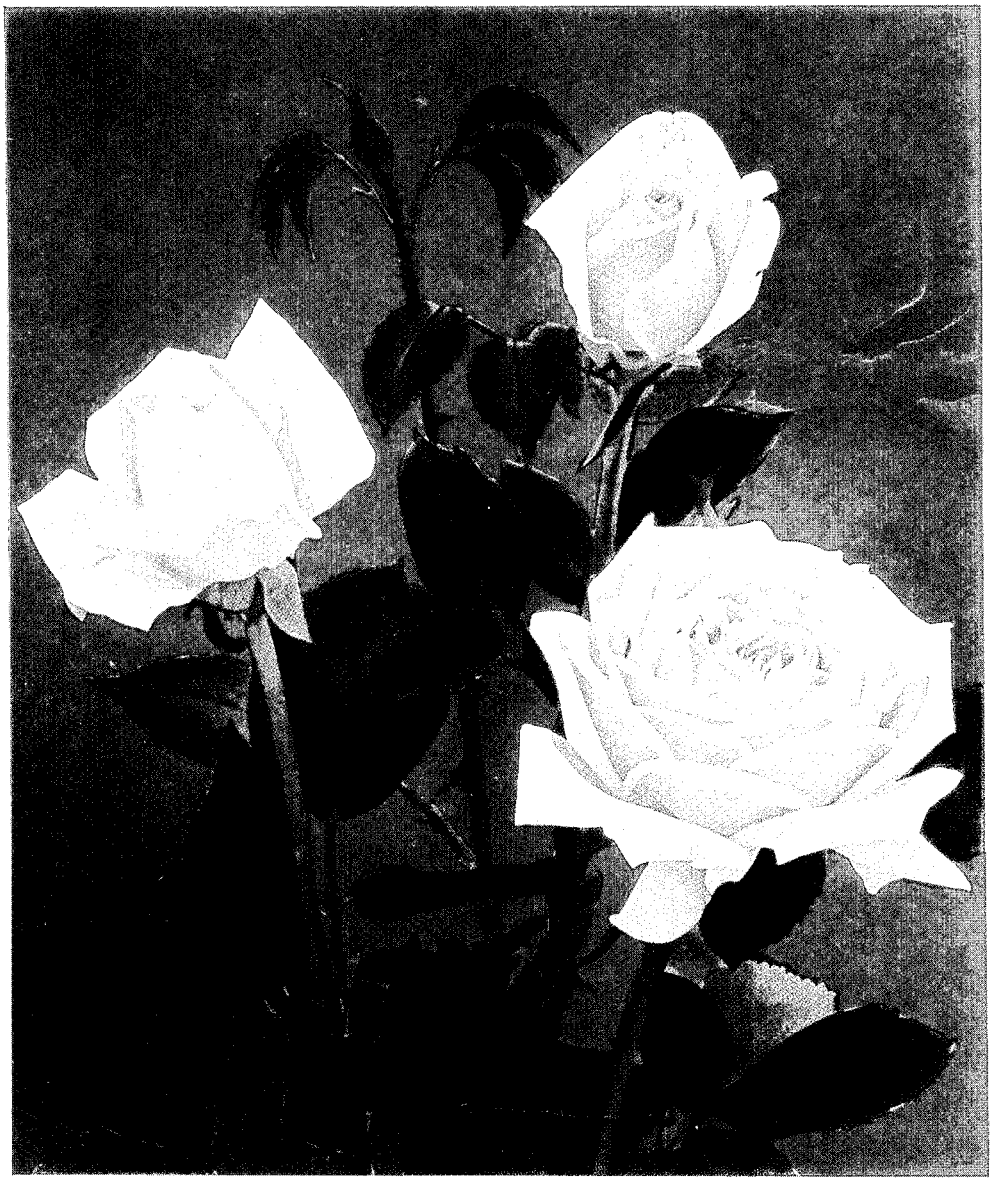
Inventor
Alexander Dickson, Jr.
By Robert Robb
Attorneys Patented Sept. 5, 1944

Plant Pat. 638

UNITED STATES PATENT OFFICE

638

ROSE PLANT

Alexander Dickson, Jr., Newtonards, Belfast, Ireland, assignor to Jackson & Perkins Company, Newark, N. Y., a corporation of New York Application April 25, 1944, Serial No. 532,637

1 Claim. (Cl. 47—61)

The present invention relates to a new and distinct variety of rose plant of the hybrid tea class, originated by crossing a deep rose colored seedling and my prior introduction "Lucie Marie."

This new rose, specimens of which are depicted in the accompanying illustration, is distinguished from its parents, both of which are characteristically of the Salmon color range, by the new pink coloring of both the buds and the open flowers. It is also characterized as to novelty by its mass of bloom in the spring season which, in this hybrid tea, resembles the mass of bloom of older hybrid perpetual roses, and by its consistent habit of steadily blooming throughout the season after the said mass spring bloom.

Other important distinctions reside in the solid stems of the plant with a minimum of pith in contrast to the stems, for example, found in the well-known variety "Dame Edith Helen"; in the great number of petals of each bloom which open perfectly throughout all the plant's blooming season; and finally in the disease resistance of its Yew Green foliage.

Asexual reproduction of the new variety shows the above characteristics to be established and fixed.

The following is a detailed description of this new variety, color terminology being in accord with Ridgway's Color Standard:

Parentage: Seedling.
- *Seed parent.*—Deep Salmon seedling.
- *Pollen parent.*—"Lucie Marie."

Classification:
- *Botanic and commercial.*—Hybrid tea.

*Flower*

(Observations made in the fields of Jackson & Perkins Company, Newark, New York, in the month of September, 1943, in the afternoon.)

Blooming habit: Recurrent—continuous. Blooms particularly heavy in early spring.

Bud:
- *Size.*—Medium.
- *Form.*—Ovoid. It is not affected by wet or hot weather.
- *Color.*—When sepals first divide—Peach Red, Plate 1. When petals begin to unfurl—Rose Doree, Plate 1. When half blown: inside of petals—between Begonia Rose, Plate 1, and Eosine Pink, Plate 1; reverse of petals—Eosine Pink, Plate 1.
- *Sepals.*—Branched, "hood" above bud. Curl back when petals begin to unfurl. Color—inside—Deep Seafoam, Plate 31; outside—Light Cress Green, Plate 31.
- *Calyx.*—Shape—apple. Size—small. Aspect—smooth. Odor when rubbed—none. Color—Cress Green, Plate 31.
- *Peduncle.* — Length — medium. Aspect — prickly. Color—Light Cress Green, Plate 31. Strength—erect; slender.
- *Opening.*—Bud opens up well; is not affected by adverse conditions.

Bloom:
- *Size*—Large; average size when fully expanded, 4½".
- *Borne.*—Singly.
- *Stems.*—Medium length; normal strength.
- *Form.*—When first open, cupped. Permanence—retains its form to the end.
- *Petalage.*—Double (full but open center). Number of petals under normal conditions, 40 to 45.
- *Color.*—Center of flower—Begonia Rose, Plate 1. Outer petals—between Eosine Pink, Plate 1, and Hermosa Pink, Plate 1. Base of petals (aiglet)—Pale Lemon Yellow, Plate 12. Inside of petals—Eosine Pink, Plate 1, overcast with Rose Pink, Plate 12. Reverse of petals—between La France, Plate 1, and Rose Pink, Plate 12. General tonality from a distance—Deep Rose Pink, Plate 12.
- *Discoloration.*—General tonality at end of first day—Begonia Rose, Plate 1, overlaid with Deep Rose Pink, Plate 12. Second day—Eosine Pink, Plate 1, overlaid with Rose Pink, Plate 12. Third day—Deep Rose Pink, Plate 12.

Petals:
- *Texture.*—Thin; is not affected by wet or hot weather.
- *Appearance.* — Inside — satiny. Outside — shiny.
- *Form.*—Oval.
- *Arrangement.*—Informal (with "rags" in center). Petaloids in center—few; small.
- *Persistence.*—Drop off cleanly.
- *Fragrance.*—Moderate. Nature—"Old Rose perfume" (Centifolia).
- *Lasting quality.*—On the plant and as cut flower—long.

Genital organs:
- *Stamens, anthers.*—Medium size; few. Color—Light Cadmium, Plate 4. Arrangement—regular around styles.

*Stamens, filaments (threads).*—Long. Color—Apricot Yellow, Plate 4.
*Pollen.*—Buff Yellow, Plate 4.
*Styles.*—Bunched, even; medium length; thin.
*Stigmas.*—Empire Yellow, Plate 4.
*Ovaries.*—Some protruding from calyx.

*Plant*

Form: Bush.
Growth: Vigorous; compact.
Foliage: 5 to 7 leaflets.
*Size.*—Large.
*Quantity.*—Abundant.
*Color.*—New foliage: upper side, center—Yellowish Oil Green, Plate 5; edges—Madder Brown, Plate 13; prominant veins, Madder Brown, Plate 13; under side—Rainette Green, Plate 31, edged and veined with Madder Brown, Plate 13. Old foliage: upper side—Yew Green, Plate 31; under side—Light Elm Green, Plate 17.
*Shape.*—Oval pointed.
*Texture.*—Upper side—glossy; under side—rough. Ribs and veins—prominent.
*Edge.*—Serrated (saw toothed).
*Serration.*—Double; sharp.
*Leaf stem.*—Light Cress Green, Plate 31. Under side—prickles.
*Stipules.*—Short; bearded.
*Disease resistance.*—Resistant insofar as this is evidenced by absence of any disease throughout development and establishment of this variety.

Wood:
*New wood.*—Color—Lettuce Green, Plate 5. Bark—smooth.
*Old wood.*—Color—Cress Green, Plate 31. Bark—smooth. Center of wood, hard, not pithy.

Thorns (thorns are divided into thorns, prickles, and short needles):
*Thorns.*—Quantity—on main stalks from base and on laterals from stalk—few. Form—narrow base; short; hooked downward. Color when young—Oxblood Red, Plate 1. Position—irregular.
*Prickles.*—Quantity—on main stalks and on laterals—none.
*Short needles.*—Quantity—on main stalks and on laterals—none.

I claim:

A new and distinct variety of rose plant of the hybrid tea class, characterized as to novelty by the pink coloring of the buds and open flowers, the great number of petals per bloom opening perfectly throughout the blooming period, the mass of bloom developed in the spring season and continuity of blooming thereafter, and the disease resistance of its Yew Green foliage, substantially as shown and described.

ALEXANDER DICKSON, Jr.